(12) United States Patent
Dakka et al.

(10) Patent No.: US 8,940,941 B2
(45) Date of Patent: Jan. 27, 2015

(54) PROCESS FOR PRODUCING PHENOL AND METHOD FOR REGENERATING CATALYST DEACTIVATED IN THE PROCESS

(71) Applicant: ExxonMobil Chemical Patents Inc., Baytown, TX (US)

(72) Inventors: Jihad Mohammed Dakka, Whitehouse Station, NJ (US); Kun Wang, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 14/094,243

(22) Filed: Dec. 2, 2013

(65) Prior Publication Data

US 2014/0163259 A1 Jun. 12, 2014

Related U.S. Application Data

(60) Provisional application No. 61/734,192, filed on Dec. 6, 2012.

(30) Foreign Application Priority Data

Feb. 11, 2013 (EP) ..................... 13154755

(51) Int. Cl.
| | |
|---|---|
| C07C 45/51 | (2006.01) |
| C07C 37/08 | (2006.01) |
| B01J 29/90 | (2006.01) |
| B01J 38/48 | (2006.01) |

(52) U.S. Cl.
CPC ............... B01J 29/90 (2013.01); C07C 37/08 (2013.01); C07C 45/517 (2013.01); B01J 38/48 (2013.01)
USPC .......................................... 568/376; 568/798

(58) Field of Classification Search
USPC ................................. 568/376, 798
See application file for complete search history.

(56) References Cited

U.S. PATENT DOCUMENTS

| | | | |
|---|---|---|---|
| 4,439,409 A | 3/1984 | Puppe et al. | |
| 4,490,565 A * | 12/1984 | Chang et al. ................. | 568/798 |
| 4,954,325 A | 9/1990 | Rubin et al. | |
| 5,236,575 A | 8/1993 | Bennett et al. | |
| 5,250,277 A | 10/1993 | Kresge et al. | |
| 5,258,555 A * | 11/1993 | Pinkos et al. ................. | 568/835 |
| 5,362,697 A | 11/1994 | Fung et al. | |
| 6,037,513 A | 3/2000 | Chang et al. | |
| 6,049,018 A | 4/2000 | Calabro et al. | |
| 6,077,498 A | 6/2000 | Diaz Cabañas et al. | |
| 6,169,216 B1 * | 1/2001 | Levin et al. ................. | 568/798 |
| 6,297,406 B1 | 10/2001 | Levin et al. | |
| 6,403,514 B1 * | 6/2002 | Mantegazza et al. ........... | 502/22 |
| 6,441,251 B1 * | 8/2002 | Levin et al. ................. | 568/798 |
| 6,720,462 B2 | 4/2004 | Kuhnle et al. | |
| 6,756,030 B1 | 6/2004 | Rohde et al. | |
| 2012/0157718 A1 * | 6/2012 | Bencini et al. ................ | 568/342 |

FOREIGN PATENT DOCUMENTS

| | | |
|---|---|---|
| EP | 0 293 032 | 11/1988 |
| JP | 2007-099745 | 4/2007 |
| SU | 266 736 | 4/1970 |
| WO | WO 97/17290 | 5/1997 |
| WO | WO 00/64849 | 11/2000 |
| WO | WO 2009/025939 | 2/2009 |
| WO | WO 2010/042269 | 4/2010 |
| WO | WO 2011/001244 | 1/2011 |
| WO | WO 2012/145028 | 10/2012 |

OTHER PUBLICATIONS

Ishida, H., "Liquid-phase hydration process of cyclohexene with zeolites," Catalysis Surveys from Japan 1 (1997), pp. 241-246, Baltzer Science Publishers BV.
Kono et al., "Liquid-Phase Hydration of Cyclohexene with Highly Siliceous Zeolites," Nippon Kagaku Kaishi, The Chemical Society of Japan, vol. 1989 (1989), No. 3, pp. 521-527.
Periodic Table of the Elements, Chemical and Engineering News, vol. 63, No. 5, p. 27 (1985).

* cited by examiner

Primary Examiner — Sikarl Witherspoon
(74) Attorney, Agent, or Firm — Stephen A. Bashi; Siwen Chen (57) ABSTRACT

A process for producing phenol is described in which a feed comprising alkylbenzene hydroperoxide is contacted with a cleavage catalyst under cleavage conditions effective to convert at least part of the hydroperoxide into phenol, the process is characterized in that at least a part of the deactivated catalyst is regenerated using a oxidizing material comprising hydrogen peroxide and then return to the process. A method of regenerating the cleavage catalyst is also described.

24 Claims, 1 Drawing Sheet

PROCESS FOR PRODUCING PHENOL AND METHOD FOR REGENERATING CATALYST DEACTIVATED IN THE PROCESS

PRIORITY CLAIM TO RELATED APPLICATIONS

This application claims priority to U.S. Provisional Application Ser. No. 61/734,192 filed Dec. 6, 2012, and European Application No. 13154755.6 filed Feb. 11, 2013, the disclosures of which are fully incorporated herein by their reference.

FIELD

The present invention relates to a method for regenerating a deactivated catalyst, and to a process for producing phenol and/or cyclohexanone.

BACKGROUND

Phenol is an important product in the chemical industry and is useful in, for example, the production of phenolic resins, bisphenol A, ε-caprolactam, adipic acid, and plasticizers.

Currently, the routes for the production of phenol include a cleavage process of alkylbenzene hydroperoxide to phenol with co-production of corresponding ketones. A common route is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide (CHP). The third step is the cleavage of the cumene hydroperoxide desirably in the presence of a sulfuric acid catalyst into equimolar amounts of phenol and acetone, a co-product.

It is known that phenol and cyclohexanone can be co-produced by a variation of the Hock process in which cyclohexylbenzene is oxidized to obtain cyclohexylbenzene hydroperoxide (CHBHP), and the hydroperoxide is decomposed in the presence of an acid catalyst to the desired phenol and cyclohexanone. U.S. Pat. No. 6,037,513 discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt, and mixtures thereof. The reference also discloses that the resultant cyclohexylbenzene can be oxidized to the corresponding hydroperoxide which is then decomposed to the desired phenol and cyclohexanone co-product.

It is also known that phenol and methyl ethyl ketone can be co-produced by a variation of the Hock process in which sec-butylbenzene is oxidized to obtain sec-butylbenzene hydroperoxide (SBBHP), and the hydroperoxide is cleaved in the presence of an acid catalyst to desired phenol and methyl ethyl ketone, such as that disclosed in International Publication No. WO2010/042269.

In most processes for cleavage of alkylbenzene hydroperoxide to phenol, sulfuric acid is the main catalyst. However, there are some disadvantages of using sulfuric acid for cyclohexylbenzene hydroperoxide cleavage, for example: 1) sulfuric acid is corrosive, especially in the presence of water, requiring expensive materials for reactor construction; 2) sulfuric acid needs to be neutralized before product separation and distillation, which requires additional chemicals such as phenate, caustics, or organic amines; and 3) the salt generated from neutralization requires separation and disposal, and the waste water needs to be treated.

Existing literature include numerous suggestions for replacing sulfuric acid in the cleavage of alkylbenzene hydroperoxide. For example, U.S. Pat. No. 4,490,565 discloses that zeolite beta is an effective replacement for sulfuric acid in the cleavage of cumene hydroperoxide and indicates that the yields, conversions and selectivities are advantageously superior to those produced by the use of the large pore zeolites X and Y. In U.S. Pat. No. 4,490,566, similar improvements over the large pore zeolites X and Y are reported with intermediate pore size zeolites, such as ZSM-5. International Publication No. WO 00/64849 discloses a process for producing phenol and acetone from cumene hydroperoxide is described in which the cumene hydroperoxide is contacted with a solid-acid catalyst comprising a sulfated transition metal oxide, preferably sulfated zirconia, and it is reported such a solid-acid catalyst shows a good combination of activity and selectivity as a replacement for sulfuric acid. International Publication No. WO2011/001244 discloses that cyclohexylbenzene hydroperoxide can be converted to phenol and cyclohexanone in the presence of a variety of homogeneous or heterogeneous acid catalysts selected from Brønsted acids and Lewis acids. Suitable homogeneous catalysts are said to include protic acids selected from sulfuric acid, phosphoric acid, hydrochloric acid, and p-toluenesulfonic acid. Solid Brønsted acids such as Amberlyst and Lewis acids selected from ferric chloride, zinc chloride, and boron trifluoride are also disclosed. In addition, suitable heterogeneous acids are said to include zeolite beta, zeolite Y, zeolite X, ZSM-5, ZSM-12, and mordenite. Similarly, Japan Unexamined Publication 2007-099745 discloses that cycloalkyl benzene hydroperoxides can be cleaved with high selectivity to phenol and cycloalkanone in the presence of aluminosilicate zeolites having pore diameter of 0.6 nm or greater, such as zeolite Y and zeolite beta.

It is known that molecular sieves, especially zeolites, lose performance, such as activity, selectivity, and capacity, through various deactivation mechanisms. As the molecular sieve catalyst deactivates over time, more severe conditions, such as higher temperature and/or lower through-put, are normally required to maintain comparable activity and/or selectivity. The deactivated catalyst, at the end of its useful life, may contain a significant amount of coke, such as exceeding 1 wt %, and sometimes even as high as 50 wt %.

Solid state NMR reveals that the "coke" deposited on the cleavage catalyst is a mixture of mostly oxygenates containing one or more of alcohol, ketone, carboxylic, ester or aldehyde functionalities and fused aromatic compounds. Typically, a given coke mixture can be characterized by a given H/C mole ratio, which can be determined by burning the coke using a Temperature Program Oxidation. Usually, if the H/C ratio is less than 1, the coke is considered as "hard", otherwise it is considered as "soft". One commonly used regeneration technique to remove "hard" coke is to burn off the coke from the catalyst in an oxidative environment, such as air or oxygen, and one commonly used regeneration technique to remove "soft" coke is use of a solvent or solvent mixture, for example, an ammonium hydroxide solution to wash the spent catalyst. However, these methods are expensive, and may result in deterioration of the catalyst due to removal of aluminum from the zeolite framework by the steam formed during calcination, as well as the alkaline washing solution. Therefore, there is a need of a method for regenerating the catalyst without deterioration of the catalyst.

U.S. Pat. No. 5,258,555 discloses a process for the preparation of a cycloalkanol by the reaction of a cycloolefin with water in the presence of a solid acidic catalyst. It also discloses that when the catalyst, e.g., the zeolite, becomes deactivated after a certain reaction time, it can be regenerated by a simple method, which desirably comprises an initial rinse of the fixed bed of solid acidic catalyst with water followed by treatment with an aqueous hydrogen peroxide solution at a temperature from 50° C. to 120° C. and preferably from 65° C. to 80° C. However, in this reference, the catalyst is used in a cycloalkane hydration reaction where water is a reactant and results in cycloalkanol as a product. On the other hand, in a cleavage process of alkylbenzene hydroperoxide to phenol, water is not a reactant in the cleavage reaction of alkylbenzene hydroperoxide to phenol, and the feed typically contains hydrocarbon, hydroperoxide, oxygenates such as organic acids, ketones and alcohols, and the resulting product typically contains a large amount of oxygenates. Consequently, the catalyst deactivation mechanism and the nature of coke formed in the hydration reaction of U.S. Pat. No. 5,258,555 would be different from that in the cleavage process of alkylbenzene hydroperoxide to phenol. Therefore, one can expect the coke formed in the cleavage process would differ substantially from the coke formed in the hydration process disclosed in U.S. Pat. No. 5,258,555. For one, it is believed that coke formed in the hydration of cycloolefin to cycloalkanol would be caused by cycloolefin, and would not contain oxygenates.

There remains a need for a method for regenerating a solid acid catalyst by which the regenerated catalyst can be recycled to a non-aqueous reaction with high catalyst activity. There is also a need for a process of producing phenol in which the deactivated catalyst can be regenerated and recycled to the process without deterioration of the catalyst.

SUMMARY

We have discovered that a catalyst deactivated during cleavage of alkylbenzene hydroperoxide to phenol can be regenerated using an oxidizing material comprising hydrogen peroxide ($H_2O_2$). Unexpectedly, we have discovered that a catalyst for cleavage of alkylbenzene hydroperoxide to phenol can be regenerated using an aqueous hydrogen peroxide solution and recycled to the cleavage process, which is a substantially non-aqueous reaction. Accordingly, we have discovered a process for producing phenol from alkylbenzene hydroperoxide, comprising regenerating a deactivated cleavage catalyst using an oxidizing material comprising hydrogen peroxide, and returning the regenerated cleavage catalyst to the cleavage process.

Therefore, a first aspect of the present disclosure relates to a process for producing phenol comprising: (a) contacting a feed comprising alkylbenzene hydroperoxide with a cleavage catalyst comprising a zeolite having a FAU, *BEA, MFI, MTW, or MOR framework type, and/or a solid-acid comprising a sulfated transition metal oxide under cleavage conditions effective to convert at least part of the alkylbenzene hydroperoxide to phenol; (b) regenerating at least part of the cleavage catalyst by contacting the catalyst with an oxidizing material comprising hydrogen peroxide; and (c) returning at least part of the regenerated catalyst to step (a) after step (b).

A second aspect of the present disclosure relates to a method for regenerating a catalyst comprising a zeolite having a FAU, *BEA, MFI, MTW, or MOR framework type, and/or a solid acid comprising a sulfated transition metal oxide deactivated in a cleavage process of cyclohexylbenzene hydroperoxide to phenol and cyclohexanone, the method comprising of contacting the deactivated catalyst with an aqueous hydrogen peroxide solution under regeneration conditions including a temperature of from 50° C. to 250° C. and a pressure of from 200 kPa to 3000 kPa.

The oxidizing material comprising hydrogen peroxide may be an aqueous hydrogen peroxide solution. The aqueous hydrogen peroxide solution may have a hydrogen peroxide concentration of from 5 wt % to 50 wt % based on the weight of the aqueous solution.

The cleavage catalyst may comprise a zeolite having a FAU framework. The cleavage catalyst may be used in a process of cleaving cyclohexylbenzene hydroperoxide to phenol and cyclohexanone, or cumene hydroperoxide to phenol and acetone, or sec-butylbenzene hydroperoxide to methyl ethyl hydroperoxide.

The regeneration of the catalyst may be conducted at a temperature in a range from 50° C. to 250° C. and a pressure in a range from 200 kPa to 3000 kPa. Desirably, the regeneration is conducted at a time period of from 0.5 hour to 5 days.

The regeneration of the catalyst may be conducted wherein the weight ratio of hydrogen peroxide to the catalyst is from 0.01 to 10.0.

Desirably, the cleavage conditions comprise a temperature of from 20° C. to 200° C. and a pressure of from 100 kPa to 2000 kPa.

The process for producing phenol further can comprise: (i) contacting alkylbenzene with an oxygen-containing compound in the presence of an oxidation catalyst comprising a cyclic imide under oxidation conditions effective to produce an oxidation product comprising alkylbenzene hydroperoxide and cyclic imide catalyst; and (ii) supplying at least a portion of the oxidation product comprising alkylbenzene hydroperoxide to the feed of step (a).

In a third aspect, the present disclosure relates to a method for producing phenol and/or cyclohexanone, the process comprising: (a) hydroalkylating benzene with hydrogen in the presence of a hydroalkylation catalyst under conditions effective to produce a hydroalkylation reaction product comprising cyclohexylbenzene; (b) separating at least a portion of the cyclohexylbenzene from the hydroalkylation reaction product; (c) contacting at least a portion of the cyclohexylbenzene from the separating step (b) with an oxygen-containing compound in the presence of an oxidation catalyst comprising a cyclic imide under oxidation conditions effective to produce an oxidation product comprising cyclohexylbenzene hydroperoxide and cyclic imide catalyst; (d) contacting at least a portion of the oxidation product comprising cyclohexylbenzene hydroperoxide with a cleavage catalyst comprising a zeolite having FAU, *BEA, MFI, MTW, or MOR framework type and/or a solid acid comprising a sulfated transition metal oxide under cleavage conditions effective to convert at least part of the cyclohexylbenzene hydroperoxide into phenol and/or cyclohexanone; (e) regenerating at least part of the cleavage catalyst deactivated in step (d) by contacting the catalyst with an aqueous hydrogen peroxide solution; and (f) returning at least part of the regenerated catalyst to step (d) after step (e).

Additional features and advantages of the invention will be set forth in the detailed description and claims, as well as the appended drawings. It is to be understood that the foregoing general description and the following detailed description are merely exemplary of the invention, and are intended to provide an overview or framework to understanding the nature and character of the invention as it is claimed.

DETAILED DESCRIPTION

In the present disclosure, a process may be described as comprising of at least one "step." It should be understood that each step is an action or operation that may be conducted once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, some steps may be conducted simultaneously, for example, in the same reaction zone. Preferably, the steps are performed in the order listed.

Unless otherwise indicated, all numbers in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise.

As used herein, the term "cyclohexylbenzene" shall mean benzene substituted by a single cyclohexyl group, unless specified to the contrary or the context clearly indicates otherwise. As used herein, the generic term "dicyclohexylbenzene" shall include 1,2-dicyclohexylbenzene, 1,3-dicyclohexylbenzene, 1,4-dicyclohexylbenzene, and mixtures and combinations of at least two thereof in any proportion. As used herein, the generic term "tricyclohexylbenzene" shall include 1,2,3-tricyclohexylbenzene, 1,2,4-tricyclohexylbenzene and 1,3,5-tricyclohexylbenzene, and combinations and mixtures thereof at any proportion. The generic term "polycycloyhexylbenzene" shall include any of the dicyclohexylbenzene isomers and tricyclohexylbenzene isomers described above, and combinations and mixtures of at least two thereof in any proportion.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated to the contrary. All ranges expressed herein should include both end points as two specific embodiments unless specified or indicated to the contrary.

Described herein includes a process for producing phenol by cleavage of alkylbenzene hydroperoxide in the presence of a catalyst comprising a zeolite having a FAU, *BEA, MTW, or MOR framework type, and a method for regenerating a catalyst deactivated in a cleavage process of alkylbenzene hydroperoxide to phenol.

The alkylbenzene hydroperoxide may be produced by oxidation of a corresponding akylbenzene compound. Examples of suitable alkylbenzene compounds which are made to their corresponding hydroperoxides include cumene, sec-butylbenzene, p-methyl-sec-butylbenzene, 1,4-diphenylcyclohexane, sec-pentylbenzene, sec-hexylbenzene, cyclopentylbenzene, cyclohexylbenzene and cyclooctylbenzene. Exemplary alkylbenzene hydroperoxides include cumene hydroperoxide, sec-butylbenzene hydroperoxide, and cylclohexylbenzene hydroperoxide.

Production of phenol by cleavage of cyclohexylbenzene hydroperoxide will be mainly described herein, but the present disclosure can be equally applicable to the production of phenol from other alkylbenzene hydroperoxide described herein, such as cleavage of cumene hydroperoxide to phenol and aceton, or cleavage of sec-butylbenzene hydroperoxide to phenol and methyl ethyl ketone.

The cleavage process can form part of an integrated process for producing phenol and cyclohexanone from benzene, wherein the benzene is converted to cyclohexylbenzene; the cyclohexylbenzene is then oxidized to cyclohexylbenzene hydroperoxide; the cyclohexylbenzene hydroperoxide is cleaved to produce phenol and cyclohexanone; the cleavage catalyst, deactivated over time, is regenerated using an oxidizing material comprising hydrogen peroxide, especially an aqueous hydrogen peroxide solution; and the regenerated catalyst is then returned to the step of cleavage of cyclohexylbenzene hydroperoxide. The present process will now be more particularly described with reference to this particular integrated process.

Production of the Cyclohexylbenzene

In an initial step starting from benzene, cyclohexylbenzene is produced by reacting benzene with cyclohexene in the presence of a catalyst having an alkylation function and under conditions to promote the following reaction:

The cyclohexene can be supplied to the reaction zone as a separate feed from the benzene, but normally it is produced in situ by selective hydrogenation of the benzene in the presence of a hydrogenation component provided on the catalyst having the alkylation function. The bifunctional catalyst is therefore referred to herein as a hydroalkylation catalyst, and overall the hydroalkylation reaction proceeds as follows to produce cyclohexylbenzene (CHB):

Any commercially available benzene feed can be used in the hydroalkylation step, but preferably the benzene has a purity level of at least 99 wt %. Similarly, although the source of hydrogen is not critical, it is desirable that the hydrogen is at least 99 wt % pure.

Conveniently, the total feed to the hydroalkylation step contains less than 1000 ppm, such as less than 500 ppm, for example less than 100 ppm, of water. In addition, the total feed can contain less than 100 ppm, such as less than 30 ppm, for example less than 3 ppm, sulfur and less than 10 ppm, such as less than 1 ppm, for example less than 0.1 ppm, of nitrogen.

Hydrogen can be supplied to the hydroalkylation step over a wide range of values, but is desirably arranged such that the molar ratio of hydrogen to benzene in the hydroalkylation feed is between about 0.15:1 and about 15:1, such as between about 0.4:1 and about 4:1, for example between about 0.4:1 and about 0.9:1.

In addition to benzene and hydrogen, a diluent, which is substantially inert under hydroalkylation conditions, may be supplied to the hydroalkylation reaction. The diluent can be a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, the diluent is desirably added in an amount such that the weight ratio of the diluent to the aromatic compound is at least 1:100, for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth Edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Desirably, the amount of hydrogenation metal present in the catalyst is between about 0.05 wt % and about 10 wt %, such as between about 0.1 wt % and about 5 wt %, of the catalyst. Where the MCM-22 family molecular sieve is an aluminosilicate, the amount of hydrogenation metal present can be such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in some advantageous examples, at least 50 wt %, for example at least 75 wt %, and desirably substantially all of the hydrogenation metal is supported on an inorganic oxide separate from, but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. The catalyst composite can be produced by co-pelletization, in which a mixture of the molecular sieve and the metal-containing inorganic oxide are formed into pellets at high pressure (desirably about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays, or others in which the main mineral constituent is halloysite, kaolinite, dickite, nacrite, or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene, or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is desirably conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio about of 1:1 to about 5:1.

Dealkylation or cracking is also desirably effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Desirably, the acid catalyst includes at least one aluminosilicate, aluminophosphate, or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is desirably from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise of at least one metal selected from Groups 6 to 10 of the Periodic Table of Elements, such as platinum, palladium, and compounds and mixtures thereof. Desirably, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Desirably, the promoter is present in an amount between about 0.1 wt % and about 5 wt % of the catalyst. Suitable dehydrogenation conditions include a temperature of about 250° C. to about 500° C., a pressure of about atmospheric to about 14.5 psig to 500 psig (100 kPa to 3550 kPa), a weight hourly space velocity of about 0.2 hr$^{-1}$ to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene, and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air, or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N''-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N''-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. The oxidation reactor may have means to withdraw and pump a portion of its contents through a suitable cooling device and return the cooled portion to the reactor, thereby managing the heat generated in the oxidation reaction. Alternatively, cooling coils providing indirect cooling, say by cooling water, may be conducted within the oxidation reactor to remove the generated heat. The oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Desirably, the product of the cyclohexylbenzene oxidation reaction, the oxidation product, contains at least 5 wt %, such as at least 10 wt %, for example at least 15 wt %, or at least 20 wt % cyclohexyl-1-phenyl-1-hydroperoxide based upon the total weight of the oxidation product. Generally, the oxidation product contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation product. The oxidation product may further comprise imide catalyst and unreacted cyclohexylbenzene. For example, the oxidation product may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation product.

At least a portion of the oxidation product is then subjected to a cleavage reaction, either directly or after undergoing prior separation or treatment. For example, all or a fraction of the oxidation product may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary, nor preferred. Additionally or alternatively, all or a fraction of the oxidation product, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the above-treated oxidation product reduced or free from imide oxidation catalyst may be subjected to the cleavage reaction.

As another example, all or a fraction of the oxidation product may be subjected to water washing and then passage through an adsorbent, such as a 3A molecular sieve, to separate water and other adsorbable compounds, and provide a treated oxidation product with reduced water or imide content that may be subjected to the cleavage reaction. Similarly, all or a fraction of the oxidation product may undergo a chemically or physically based adsorption, such as passage over a bed of sodium carbonate to remove the imide oxidation catalyst (e.g., NHPI) or other adsorbable components, and provide a treated oxidation product reduced in oxidation catalyst or other adsorbable component content that may be subjected to the cleavage reaction. Another possible separation involves contacting all or a fraction of the oxidation product with a liquid containing a base, such as an aqueous solution of an alkali metal carbonate or hydrogen carbonate, to form an aqueous phase comprising a salt of the imide oxidation catalyst, and an organic phase reduced in imide oxidation catalyst.

An example of separation by basic material treatment is disclosed in International Publication No. WO 2009/025939, the entire contents of which are incorporated herein by reference.

Alternatively and additionally, all or a fraction of the oxidation product may be contacted with an aluminosilicate zeolite of the FAU type to reduce the amount of unreacted imide catalyst in the product by adsorption onto the zeolite. The FAU type zeolite employed to remove the oxidation catalyst may be same as the FAU type zeolite employed in the cleavage reaction, for example, having a unit cell size less than 24.50 Å, or less than 24.45 Å, or less than 24.40 Å, or less than 24.35 Å, such as less than 24.30 Å, and the contacting to remove the oxidation catalyst can be conducted prior to or concurrently with the cleavage reaction. The adsorbed imide catalyst can be desorbed from the FAU type zeolite by washing with a polar solvent, such as acetone or cyclohexanone, and recovered by flashing off the solvent and/or by recrystallization. The recovered imide can then be recycled to the oxidation reaction.

Hydroperoxide Cleavage

Another step in the conversion of the cyclohexylbenzene into phenol and cyclohexanone involves the acid-catalyzed cleavage of the cyclohexyl-1-phenyl-1-hydroperoxide produced in the oxidation step.

The acid catalyst used in the present cleavage reaction may comprise a zeolite having a FAU, *BEA, MTW, or MOR framework type, and/or a solid-acid comprising a sulfated transition metal oxide. The framework type as used herein is as described in the *Atlas of Zeolite Framework Types*, Ch. Baerlocher et al. (6th Ed. 2007). Illustrative zeolites having a FAU framework may include zeolite X and zeolite Y. Illustrative zeolites having *BEA framework type may include a zeolite beta. Illustrative zeolites having MTW framework type may include ZSM-12. Illustrative zeolites having MOR framework type may include mordenite. The following description will be made using FAU-type zeolite, and one skilled in the art would understand that the other framework-type zeolite will be equally applicable in the cleavage process.

Solid-acid catalysts useful in the cleavage process include those comprising a sulfated transition metal oxide, such as sulfated zirconia, together with an oxide of iron or oxides of iron and manganese, as described in U.S. Pat. No. 6,169,216, as well as those comprising a mixed oxide of cerium and a Group IVB metal, e.g., zirconium, described in U.S. Pat. No. 6,297,406. The entire disclosure of each of the above patents is incorporated herein by reference. Such a catalyst may also comprise an oxide of a Group IVB metal, such as zirconia or titania, modified with an oxyanion or oxide of a Group VIB metal, such as an oxyanion of chromium, molybdenum, or tungsten.

When a FAU-type zeolite is used, it may have a unit cell size less than 24.5 angstroms ("Å"), such as less than or equal to 24.45 Å, or less than or equal to 24.40 Å, or less than or equal to 24.35 Å, or less than or equal to 24.30 Å, or less than or equal to 24.25 Å. The zeolite can be used in unbound form or can be combined with a binder, such as silica or alumina, such that the overall catalyst (zeolite plus binder) comprises from about 5 wt % to about 95 wt % of the zeolite.

The cleavage catalyst may have a pore volume as measured by nitrogen ($N_2$) adsorption of greater than 0.3 cc/g, or greater than 0.4 cc/g, or greater than 0.5 cc/g. The cleavage catalyst may contain less than 6 wt %, or less than 3 wt %, or less than 1 wt %, or less than 0.5 wt % of Group 3 to Group 12 metals including the lanthanide series, based upon the weight of the catalyst.

The cleavage reaction using the FAU-type zeolite catalyst may have a catalyst activity of greater than 30%, or greater than 50%, or greater than 70%, or greater than 90%, or greater than 95%, or greater than 99%, or even 100%. The phenol selectivity may be greater than 60%, or greater than 70%, or greater than 90%, or greater than 95%. The cyclohexanone selectivity may be greater than 27%, or greater than 50%, or greater than 70%, or greater than 80%, or greater than 85%, or greater than 90%. As used herein, "catalyst activity" can also refer to cyclohexylbenzene hydroperoxide conversion, which means the amount of cyclohexylbenzene hydroperoxide converted to any product. "Phenol selectivity" is relative to the theoretical phenol selectivity based upon the amount of cyclohexylbenzene hydroperoxide converted. "Cyclohexanone selectivity" is relative to the theoretical cyclohexanone selectivity based upon the amount of cyclohexylbenzene hydroperoxide converted.

Generally, the cleavage reaction is conducted under conditions including a temperature of about 20° C. to about 200° C., such as about 40° C. to about 120° C. and a gauge pressure of about 200 kPa to about 2000 kPa, such as about 200 kPa to about 1000 kPa, such that a cleavage reaction mixture, including the oxidation product fed to the cleavage reaction, can be completely or predominantly in the liquid phase during the cleavage reaction. The weight hourly space velocity may be about 1 $hr^{-1}$ to about 1000 $hr^{-1}$ on total feed, preferably from 1 $hr^{-1}$ to about 500 $hr^{-1}$, and more preferably from about 1 $hr^{-1}$ to 300 $hr^{-1}$.

The cleavage reaction can be conducted in a variety of reactor configurations and in either a single reactor or in a plurality of reactors. For example, the reaction may be conducted in at least a first reactor and a second reactor connected in series, with the first reactor being operated at a temperature of about 20° C. to about 120° C., and a pressure of about 100 kPa, gauge to about 500 kPa, gauge and the second reactor being operated at a temperature of about 40° C. to about 180° C. and a pressure of about 100 kPa, gauge to about 1000 kPa, gauge. The first and second reactors may be the same or different.

The cleavage reaction can be conducted in a slurry reactor, such as a stirred tank, pump-around loop or other suitable configuration. In one example, at least part of the cleavage reaction is conducted in a continuous stirred tank reactor (CSTR), with the catalyst being slurried in the cleavage reaction medium. Desirably, the catalyst is added in an amount between about 50 wppm and about 20,000 wppm of the cleavage reaction medium. Advantages for this configuration include easy heat management and flexibility to add/withdraw catalyst to maintain conversion as the catalyst deactivates.

The catalyst can also be used in a fixed bed plug-flow reactor with or without firstly removing the imide catalyst from the cleavage feed stream, namely the oxidation product. If the imide catalyst is not removed, the FAU bed adsorbs it, allowing its recovery and recycle to the oxidation process. In such a process design, two or more parallel cleavage reactor trains may be deployed to enable uninterrupted processing of the peroxide feed. Thus, as the FAU catalyst is saturated with the imide catalyst and/or coke causing it to deactivate in one reactor train, the cleavage feed is switched to another reactor train that contains fresh or regenerated catalyst.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. An exemplary polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

The cleavage reaction mixture may include cyclohexylbenzene hydroperoxide in an amount of at least 50 wt %, or at least 60 wt %, or at least 65 wt %, or at least 70 wt %, or at least 80 wt %, or at least 90 wt %, based upon total weight of the cleavage reaction mixture.

The major products of the cleavage reaction are phenol and cyclohexanone, each of which generally constitutes about 40 wt % to about 60 wt %, or about 45 wt % to about 55 wt % in the cleavage reaction product, such wt % being based on the weight of the cleavage reaction product exclusive of unreacted cyclohexylbenzene hydroperoxide and acid catalyst.

Catalyst Regeneration

The cleavage catalyst deactivates due to, among others, formation of coke over time. As a result, catalytic activity in terms of conversion and/or selectivity decreases over time. As used herein, a "deactivated catalyst" is a catalyst the catalytic activity of which has decreased after a certain service period to an undesirable level. The deactivated catalyst in the process of the present disclosure may be regenerated under regeneration conditions using an oxidizing material comprising hydrogen peroxide.

The oxidizing material comprising hydrogen peroxide may be a hydrogen peroxide solution, such as an aqueous solution. It has been discovered that the catalyst regenerated using aqueous hydrogen peroxide solution can be returned to the cleavage process (a non-aqueous reaction), without affecting the conversion of cyclohexylbenzene hydroperoxide and the selectivity to phenol and cyclohexanone in the cleavage process. Without intending to be bound by a particular theory, it is believed that, surprisingly, trace amount of water on the catalyst can be helpful in improving selectivity to phenol and cyclohexanone. The oxidizing material comprising hydrogen peroxide may comprise other oxidizing material, such as ozone, molecular oxygen, air or peroxo compounds such as peroxosulfates.

The aqueous hydrogen peroxide solution may have a hydrogen peroxide concentration in a range from 0.1 wt % to 50 wt % based on the weight of the solution. For example, the hydrogen peroxide concentration can be in a range from a low of C1 wt % to a high of C2 wt %, where C1 can be 1.0, 2.0, 3.0, 5.0, 8.0, 10, 12, 15, 20, 25, and C2 can be 50, 45, 40, 35, 30, 25, 20, 15, 12, or even 10, to the extent C1<C2.

The deactivated catalyst can be regenerated under regeneration conditions comprising: (I) a temperature in a range from a low of T1° C. to a high of T2° C., where T1 can be 50, 60, 70, 80, 90, 100, 110, 120, 130, 140, 150, and T2 can be 250, 240, 230, 220, 210, 200, 190, 180, 170, 160, or even 150, to the extent T1<T2; and (II) a pressure in a range from a low of P1 kPa to a high of P2 kPa, where P1 can be 200, 250, 300, 350, 400, 450, 500, and P2 can be 3000, 2500, 2000, 1500, or 1000, to the extent P1<P2. When using the aqueous hydrogen peroxide solution to regenerate the deactivated catalyst, the solution may be used in an amount such that the weight ratio of hydrogen peroxide to the deactivated catalyst is in a range from WR1 to WR2, where WR1 can be 0.01, 0.02, 0.05, 0.08, 0.10, 0.15, 0.20, 0.25, 0.30, 0.40, 0.50, 0.60, 0.70, 0.80, 0.90, 1.0, and WR2 can be 10, 9.0, 8.0, 7.0, 6.0, 5.0, 4.0, 3.0, 2.0, or 1.0, to the extent WR1<WR2. The weight hourly space velocity of the aqueous hydrogen peroxide solution can be in a range from WRSV1 to WRSV2, where WRSV1 can be 0.1, 0.5, 1.0, 2.0, 3.0, 5.0, 8.0, 10, 15, 20, and WRSV2 can be 100, 90, 80, 70, 60, 50, 40, 30, 20, to the extent WRSV1<WRSV2.

The time period for regeneration can vary depending on the amount of coke deposited on the catalyst, the nature of the coke, the hydrogen peroxide concentration of the solution, and other regeneration conditions. The regeneration can be conducted for a time period in a range of D1 hours to D2 hours, where D1 can be 0.1, 0.2, 0.3, 0.4, 0.5, 0.8, 1.0, 2.0, 3.0, 4.0, 5.0, 8.0, 10.0, and D2 can be 240, 196, 144, 120, 96.0, 72.0, 60.0, 48.0, 36.0, or 24.0. The regeneration may be conducted at reflux conditions, and at the end of the regeneration the regenerated catalyst can be separated and reclaimed by simple filtration followed by optional drying.

The deactivated catalyst comprises of coke deposited on the catalyst before regeneration in the amount in a range from Ck1 wt % to Ck2 wt %, based on the total weight of the deactivated catalyst and the coke, where Ck1 can be 0.1, 0.2, 0.3, 0.4, 0.5, 1, 3, 5, 8, 10, 12, 14, 15, and Ck2 can be 50, 45, 40, 35, 30, 25, 20, 15, to the extent Ck1<Ck2. In one example, after regeneration using the oxidizing material comprising hydrogen peroxide, at least 10%, such as 15%, 20%, 25%, 30%, 40%, 50%, 60%, 70%, 80%, 90%, or even 95% of the coke based on the weight of the coke deposited on the catalyst before regeneration can be removed.

The regenerated catalyst may have a catalyst activity and/or phenol selectivity comparable to a fresh catalyst, which has never been deactivated. This indicates that both the hard and soft cokes on the deactivated catalyst are removed at least partly. The silicon and aluminum on the catalyst may be rearranged after regeneration, resulting in improvement of the catalyst activity and/or phenol selectivity. The regenerated catalyst may have a catalyst activity of from 50% to 120%, such as from 70% to 100%, or from 90% to 100% of a fresh catalyst, where the catalyst activity is defined as the conversion of alkylbenzene hydroperoxide to phenol under cleavage conditions including a temperature of about 20° C. to 200° C. and a pressure of 200 kPa to 2000 kPa. The regenerated catalyst may have a selectivity to phenol of from 70% to 110%, such as from 80% to 100%, or from 90% to 100% of a corresponding fresh catalyst, where the catalyst selectivity is measured by determining the selectivity of phenol under cleavage conditions including a temperature of about 20° C. to 200° C. and a pressure of 200 kPa to 2000 kPa. The high activity of the regenerated catalyst according to the process of the present disclosure demonstrates the effectiveness of the process without having to resort to traditional high-temperature burning and high-alkalinity leaching. It is believed that, due to the relatively low regeneration temperature and near neutrality of the regeneration treatment of the present disclosure, the composition and structure of the regenerated catalyst is substantially unaltered. This makes it possible to regenerate the catalyst multiple times after multiple service cycles in the cleavage reactor.

If peroxide cleavage is performed with the oxidation product containing the imide catalyst, the latter may adsorb onto the catalyst, inhibiting its performance. In this case, regeneration using oxidizing material comprising hydrogen peroxide may be advantageously performed after recovering the adsorbed catalyst. The imide catalyst adsorbed on the catalyst can be removed or recovered by recovering the imide-loaded catalyst from the cleavage reactor, and washing this spent catalyst with a polar solvent such as acetone, methanol, ethanol, or cyclohexanone to recover its imide adsorbing capacity, as well as cleavage. The imide catalyst recovered can be re-used for oxidation.

In a slurry cleavage process, the catalyst can be regenerated on various schedules. Advantageously, the catalyst can be continuously withdrawn from the cleavage reactor, regenerated in an external recycle loop, and then returned into the cleavage reactor. Under such operation regime, a steady state of catalyst activity can be maintained through regeneration and by continuously replacing a fraction of the recycled catalyst with fresh catalyst.

In a fixed bed plug-flow reactor, the catalyst can be regenerated before the regenerated reactor train is returned to cleavage operation to replace the previously operating reactor train that can now be taken off-line for regeneration. This cycle then can be repeated until the catalyst in one or more reactor trains can no longer be regenerated to acceptable levels. In such cases, the exhausted catalyst can simply be replaced with a fresh charge before returning the train to cleavage operations.

Uses of Cyclohexanone and Phenol

Cyclohexanone produced through the processes disclosed herein may be used, for example, as an industrial solvent, as an activator in oxidation reactions and in the production of adipic acid, cyclohexanone resins, cyclohexanone oxime, caprolactam and nylons, such as nylon 6 and nylon 6,6.

Phenol produced through the processes disclosed herein may be used, for example, to produce phenolic resins, bisphenol A, ε-caprolactam, adipic acid, and/or plasticizers.

The invention will now be more particularly described with reference to the following non-limiting examples and the accompanying drawings.

Example 1

Oxidation of Cyclohexylbenzene

An amount of 631 g of cyclohexylbenzene (TCI America, Inc.) was added to a 1-liter four-necked glass flask, toward which 0.6702 g of N-hydroxyphthalimide (NHPI) (TCI America, Inc.) was added. The flask was then fitted with a reflux condenser, a mechanical stirrer, a gas sparger, and a thermometer. An air flow of 250 cc/min was bubbled through the liquid via the gas sparger; and the contents heated at 110° C. with stirring (560 rpm) for 6 hours. The flask was allowed to cool to room temperature, and the oxidation product was recovered. Gas Chromatography (GC) analysis indicated that the product contained 17.9 wt % of cyclohexylbenzene hydroperoxide (CHBHP).

Example 2

Cleavage of CHBHP using Faujasite in Fixed-Bed Operation

Figure 1:
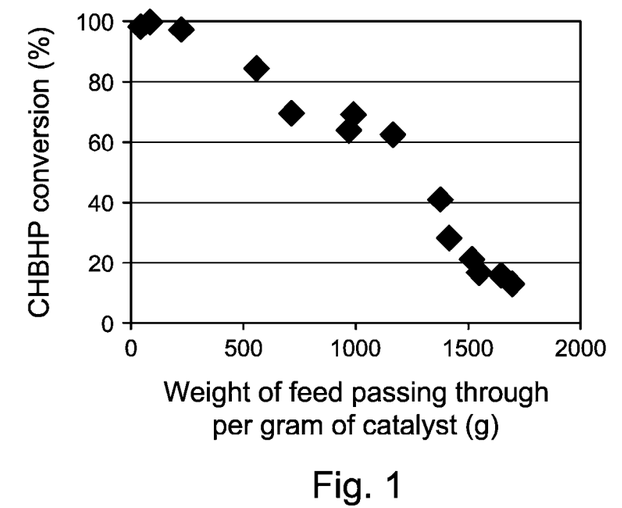
FIG. 1 shows catalyst activity as a function of amount of feed in grams having passed through per gram of catalyst over time of a fresh catalyst in the cleavage of cyclohexylbenzene hydroperoxide to phenol and cyclohexanone in Example 2.

The CHBHP from Example 1 was diluted with CHB and dodecane (internal standard) to produce a feed containing about 4 wt % CHBHP. An amount of 0.25 g of Faujasite catalyst (CBV760, a Zeolite Y catalyst available from Zeolyst International) was diluted with quartz chips to 5 cc volume, and loaded into the center zone of a ⅜" (1 cm) diameter tubular reactor. The catalyst was first dried with flowing $N_2$ at 200° C., and then cooled down to 50° C. The CHBHP feed was fed to the reactor via a pump supplied by ISCO Industries at a liquid pressure of 100 psig (790 kPa). The cleavage catalyst was deactivated with time. FIG. 1 shows the conversion of CHBHP as a function of amount of feed in grams having passed through per gram of the catalyst over time for the catalyst in the reactor. Catalyst activity and selectivity to phenol and cyclohexanone of the catalyst are shown in Table 1. At the end of the reaction, the reactor was flushed with hexanes, dried under flowing $N_2$, and the spent catalyst was separated from the reactor. TGA analysis was done, and the results indicated that the catalyst had 1.38 wt % of coke.

Example 3

Treatment of Deactivated Faujasite using Hydrogen Peroxide 0.15 g the spent catalyst from Example 2 was treated with 1 g aqueous hydrogen peroxide solution having an $H_2O_2$ concentration of 30% at reflux conditions (100° C.) for 3 hours. At the end of the reaction period, the catalyst was separated from the liquid by filtration, and the filtered catalyst was dried in an oven at 120° C. in air overnight. TGA analysis was made to the treated catalyst, and the results indicated that the catalyst had 0.59 wt % of coke. This indicated that about 60 wt % of the coke, based on the original weight of the coke deposited on the deactivated catalyst before regeneration, was removed from the deactivated catalyst after the hydrogen peroxide treatment, and was successfully regenerated.

Example 4

Figure 2:
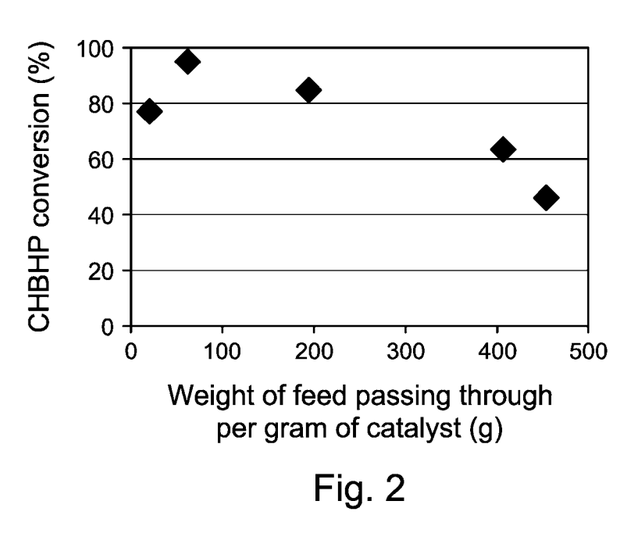
FIG. 2 shows catalyst activity as a function of the amount of feed in grams having passed through per gram of catalyst over time of a catalyst regenerated using aqueous hydrogen peroxide solution in the cleavage of cyclohexylbenzene hydroperoxide in Example 4.

Cleavage of CHBHP using Hydrogen Peroxide Treated Faujasite in Fixed-Bed Operation The hydrogen-peroxide treated catalyst from Example 3 was loaded into a fixed bed reactor (0.15 g catalyst) and was evaluated for CHBHP cleavage under the same conditions as that in Example 2. The conversion of CHBHP as a function of amount of feed in grams passed through per gram of the catalyst over time is shown in FIG. 2. Catalyst activity and selectivity to phenol and cyclohexanone of the regenerated catalyst are shown in Table 1.

Based on the FIGS. 1 and 2 and Table 1, it can be seen that the catalyst activity and selectivity to desired product was recovered by regenerating the deactivated catalyst using an oxidizing material comprising hydrogen peroxide.

TABLE 1

| Example No. | Catalyst | CHBHP Conversion (%) | Phenol Selectivity (%) | Cyclohexanone Selectivity (%) |
|---|---|---|---|---|
| 2 | Fresh | 89 | 99.3 | 95.5 |
| 4 | $H_2O_2$-regenerated | 84.5 | 93.8 | 93 |

The contents of all references cited herein are incorporated by reference in their entirety.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for producing phenol comprising:
   (a) contacting a feed comprising alkylbenzene hydroperoxide with a cleavage catalyst comprising of a zeolite having a FAU, *BEA, MTW, or MOR framework type, and/or a solid-acid comprising a sulfated transition metal oxide under non-aqueous cleavage conditions effective to convert at least part of the alkylbenzene hydroperoxide to phenol;
   (b) regenerating at least part of the cleavage catalyst by contacting the catalyst with an aqueous hydrogen peroxide solution; and
   (c) returning at least part of the regenerated catalyst to step (a) after step (b), the regenerated catalyst comprising water on the catalyst.

2. The process of claim 1, wherein the aqueous hydrogen peroxide solution has a concentration of hydrogen peroxide of from 3 wt % to 50 wt % based on the total weight of the aqueous solution.

3. The process of claim 1, wherein the cleavage catalyst comprises a zeolite having a FAU framework type.

4. The process of claim 1, wherein step (b) is conducted at a temperature of from 50° C. to 250° C.

5. The process of claim 1, wherein step (b) is conducted at a pressure of from 200 kPa to 3000 kPa.

6. The process of claim 1, wherein the weight ratio of hydrogen peroxide to the catalyst in step (b) is from 0.01 to 10.

7. The process of claim 1, wherein the catalyst in step (b) is washed with a polar solvent prior to contacting with the oxidizing material.

8. The process of claim 7, wherein the polar solvent comprises at least one of acetone, methanol, ethanol, and cyclohexanone.

9. The process of claim 1, further comprising, prior to step (a):
   (i) contacting an alkylbenzene with an oxygen-containing compound in the presence of an oxidation catalyst comprising a cyclic imide under oxidation conditions effective to produce an oxidation product comprising alkylbenzene hydroperoxide; and
   (ii) supplying at least a portion of the oxidation product to the feed of step (a).

10. The process of claim 1, wherein the alkylbenzene comprises cyclohexylbenzene, cumene, and/or sec-butylbenzene.

11. A method for regenerating a catalyst comprising contacting the catalyst with an oxidizing material comprising hydrogen peroxide, wherein the catalyst comprises a solid acid comprising a sulfated transition metal oxide deactivated in a cleavage process of alkylbenzene hydroperoxide to phenol.

12. The method of claim 11, wherein the catalyst comprises sulfated zirconia.

13. The method of claim 11, wherein the oxidizing material comprises an aqueous hydrogen peroxide solution.

14. The method of claim 13, wherein the aqueous hydrogen peroxide solution has a concentration of hydrogen peroxide of from 3 wt % to 50 wt % based on the weight of the aqueous solution.

15. The method of claim 11, wherein the catalyst is regenerated at a temperature of from 50° C. to 250° C.

16. The method of claim 11, wherein the catalyst is regenerated at a pressure of from 200 kPa to 3000 kPa.

17. The method of claim 11, wherein the weight ratio of hydrogen peroxide to the catalyst is from 0.01 to 10.

18. The method of claim 11, wherein the catalyst is regenerated for a time period of from 0.5 hour to 5 days.

19. The method of claim 11, wherein the catalyst comprises coke deposited on the catalyst before regeneration and at least 30 wt % of coke based on the weight of the coke deposited on the catalyst before regeneration is removed after regeneration.

20. The method of claim 11, wherein the regenerated catalyst has a catalyst activity of from 50% to 120% of a fresh catalyst, the catalyst activity is measured by determining the conversion of alkylbenzene hydroperoxide to phenol under cleavage conditions including a temperature of about 20° C. to 200° C. and a pressure of 200 kPa to 2000 kPa.

21. The method of claim 11, wherein the regenerated catalyst has a selectivity to phenol of from 70%-110% of a fresh catalyst, the catalyst selectivity is measured by determining the selectivity of phenol under cleavage conditions including a temperature of about 20° C. to 200° C. and a pressure of 200 kPa to 2000 kPa.

22. The method of claim 11, wherein the alkylbenzene comprises cyclohexylbenzene, cumene, or sec-butylbenzene.

23. A method for regenerating a catalyst comprising a solid acid comprising a sulfated transition metal oxide deactivated in a cleavage process of cyclohexylbenzene hydroperoxide to phenol and cyclohexanone, the method comprising contacting the deactivated catalyst with an aqueous hydrogen peroxide solution under regeneration conditions including a temperature of from 50° C. to 250° C. and a pressure of from 200 kPa to 3000 kPa.

24. A method for producing phenol and/or cyclohexanone, the process comprising:
   (a) hydroalkylating benzene with hydrogen in the presence of a hydroalkylation catalyst under conditions effective to produce a hydroalkylation reaction product comprising cyclohexylbenzene;
   (b) separating at least a portion of the cyclohexylbenzene from the hydroalkylation reaction product;
   (c) contacting at least a portion of the cyclohexylbenzene from the separating step (b) with an oxygen-containing compound in the presence of an oxidation catalyst comprising a cyclic imide under oxidation conditions effective to produce an oxidation product comprising cyclohexylbenzene hydroperoxide and cyclic imide catalyst;
   (d) contacting at least a portion of the oxidation product comprising cyclohexylbenzene hydroperoxide with a cleavage catalyst comprising a zeolite having FAU, *BEA, MTW, or MOR framework type and/or a solid acid comprising a sulfated transition metal oxide under non-aqueous cleavage conditions effective to convert at least part of the cyclohexylbenzene hydroperoxide into phenol and/or cyclohexanone;
   (e) regenerating at least part of the cleavage catalyst deactivated in step (d) by contacting the catalyst with an aqueous hydrogen peroxide solution; and
   (f) returning at least part of the regenerated catalyst to step (d) after step (e), the regenerated catalyst comprising water on the catalyst.

* * * * *